United States Patent [19]

Rousseau et al.

[11] Patent Number: 4,731,074
[45] Date of Patent: Mar. 15, 1988

[54] HEART VALVE PROSTHESIS, METHOD FOR PRODUCING A HEART VALVE PROSTHESIS AND MOULD APPLIED THEREBY

[75] Inventors: Eduard P. M. Rousseau, Maastricht; Antonius A. van Steenhoven; Joannes D. Janssen, both of Nuenen; Leonardus H. G. Wouters, Weert, all of Netherlands

[73] Assignee: Stichting voor de Technische Wetneschappen, Netherlands

[21] Appl. No.: 832,914

[22] Filed: Feb. 24, 1986

[30] Foreign Application Priority Data

Feb. 26, 1985 [NL] Netherlands ................ 8500538

[51] Int. Cl.$^4$ .............................................. A61F 2/24
[52] U.S. Cl. ...................................................... 623/2
[58] Field of Search ................ 623/2, 3, 66; 128/1 D; 525/412, 440, 445, 455

[56] References Cited

U.S. PATENT DOCUMENTS

| | | |
|---|---|---|
| 3,824,629 | 7/1974 | Shiley . |
| 4,085,165 | 4/1978 | Odaka et al. .............. 525/412 X |
| 4,222,126 | 9/1980 | Boretos et al. .................. 623/2 |
| 4,376,312 | 3/1983 | Robinson et al. ............... 623/3 |

FOREIGN PATENT DOCUMENTS 7906506 8/1979 Netherlands .

OTHER PUBLICATIONS

E. L. Gerring, et al., "Long Term Animal Trials of the Oxford Aortic/Pulmonary Valve Prosthesis Without Anticoagulants", *Trans. Amer. Soc. Artif. Int. Organs*, 1974, pp. 703–707.

G. Haussinger et al., "In-vitro Ergebnisse von Dauerfestigkeit and Hamolyse einer flexiblen Taschenklappe", *Biomedizinische Technik*, 1981, vol. 26, pp. 40–43.

R. J. Kiraly et al., *Artificial Organs*, 1981, vol. 5, pp. 323–326.

M. Ionescu, "Biological and Physical Characteristics of the Glutaraldehyde-Treated Porcine Xenografts", *Tissue Heart Valves*, 1979, pp. 178–179.

*Primary Examiner*—Richard J. Apley
*Assistant Examiner*—Alan W. Cannon
*Attorney, Agent, or Firm*—Thomas S. MacDonald; Alan H. MacPherson; Paul J. Winters

[57] ABSTRACT

Heart valve prosthesis consisting of a substantially rigid frame provided therein with several synthetic membranes whereby the membrane is a fibre-reinforced matrix material. The fibres are arranged parallel in the matrix material, and the fibre material and the matrix material are chemically identical.

17 Claims, 3 Drawing Figures

HEART VALVE PROSTHESIS, METHOD FOR PRODUCING A HEART VALVE PROSTHESIS AND MOULD APPLIED THEREBY

The invention relates to a heart valve prosthesis consisting of a substantially rigid frame provided therein with several synthetic membranes whereby the membrane is a fibre-reinforced matrix material. The invention further relates to a method for producing a heart valve prosthesis and to the mould applied thereby for producing a heart valve prosthesis intended for implantation in the aorta position, and pulmonal position consisting of a frame with three membranes provided therein.

Heart valve prostheses can be divided into three groups viz. the mechanical artificial valves, bioprostheses whereby prepared heart valves of animals are used, and artificial membrane valve prostheses. A mechanical heart valve is described in the Dutch patent application No. 7906506 and in the U.S. Pat. No. 3,824,629. A disadvantage of mechanical heart valves is that it is necessary for the patient to use anti-coagulants, which can have disadvantageous consequences in the long run. The mechanical valve namely is thrombogeneous by nature as the material of the valve is an adhering place for thrombocytes. As a result, blood coagulants arise which may interfere with the functioning of the valve and which may come loose and may have a disadvantageous effect elsewhere in the body. Therefore, it is necessary for patients with a mechanical heart valve to use anti-coagulants regularly.

With bioprostheses frequent use is made of the heart valve of a pig, but such bioprostheses have the drawback that relatively soon there occurs calcification as a result of which such a biovalve needs to be replaced again after a number of years. Such biovalves are suspended in a frame and are then implanted.

The present patent application relates to an artificial membrane valve prosthesis, which aims to be an approximation of the bioprosthesis concerning its operation, without the drawbacks of prior art bioprostheses such as the calcification of the membranes and the limited life time. For that purpose use has been made of membranes made of synthetic material suspended in a frame.

With regard to membrane valve prostheses a great deal of research has already been done and results have been published. Thus there is in Trans. Amer. Soc. Artif. Int. Organs, 1974, volume 21, pp. 703-707, according to E. L. Gerring and others, a membrane made of silicone rubber reinforced with polyester. Said polyester has been woven and afterwards provided in the silicone rubber as reinforcement. However, the valve thus obtained, known as the Oxford-valve, appeared to be insufficiently resistant to the occurring stresses. Membrane valve prostheses have been made by G. Häussinger and H. Reul as mentioned in Biomedizinische Technik, 26 (1981) pp. 40-43, whereby polyurethane, silicone rubber reinforced with a polyester web and a specific polyurethane (Avcothane-51), which is a compound of 95% polyurethane and 5% polydimethyl siloxane, have been compared. (On p. 41 of said literature reference the references to the specific materials are incorrect.) From the experiments carried out according to G. Häussinger it became apparent that the valves made of Avcothane-51 had the longest life span. It now appeared to be possible to further improve the mechanical properties of such membrane valve in accordance with the teachings of this invention.

Experiments carried out have now led to a membrane construction starting from fibre-reinforced material according to the invention which is characterised in that the fibres and arranged substantially parallel in the matrix material and the fibre material and the matrix material are chemically identical. The fibre material and the matrix material are preferably made of polyether urethane.

As the fibre material has to be more rigid than the matrix material, the basis for the preparation of the fibre material has been a polyether of a lower molecular weight than the polyether of the matrix material; therefore polyoxy tetramethylene glycol (POTM) has specifically been used, whereby for the preparation of the fibre material the polyether can first be subjected to a coupling reaction to further increase the molecular weight. The polyether urethanes are prepared in two steps. First a prepolymer is prepared from a diisocyanate and a polyether glycol in a molar compound of 2:1 and then the prepolymer chains are coupled with a chain-lengthening agent such as a diamine or diol.

The method for producing the membranes takes place in a mould, which has the shape of the membranes to be formed, in which mould the frame and the fibres are placed, and by submersing and drying the matrix material is formed around the fibres so that said fibres are embedded in the matrix material. For that purpose a film of the matrix material is preferably first applied to the mould, after which the fibres and the frame are placed in the mould wherein the fibres are placed substantially parallel to each other and perpendicular to the direction in which the membranes move in practice. Then a DMF (dimethyl formamide) solution of the matrix material is applied and the solution dried so many times that the fibres are embedded and incorporated in the matrix material so that a membrane is obtained consisting of fibre-reinforced matrix material adhered to the frame. Such a mould is known and described in Artificial Organs, volume 5 (suppl), 1981, pp. 323-326 by R. J. Kiraly and others. The mould now used has been modified as regards the specific dimensions and parameters.

The invention will be more fully explained with reference to the following description and the appended drawings, in which.

Figure 1:
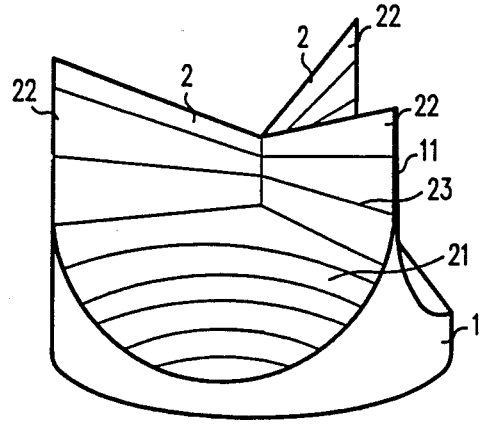
FIG. 1 is a diagrammatic view of a symmetric heart valve prosthesis with three synthetic fibre-reinforced membranes in closed position.

At the basis of the present invention is a design study for achieving an optimum design of a leaflet or membrane valve prosthesis. With a view to inexpensive production, the simplest possible valve geometry and material properties of the frame and the artificial membranes are desired and the membranes are connected directly to the frame, which was chosen flexible as a starting point for the design study in order to approximate the properties of the natural valve as much as possible. It is apparent from the literature on this field of the art that a rigid frame has a disadvantageous effect on the operation and the life time of a bioprosthesis, particularly with respect to synthetic frame and natural membranes.

The membranes are fibre-reinforced, as this is also the case in the natural situation. According to the invention, however, fibres extending substantially parallel at a distance are applied in the membranes.

Furthermore the frame legs (reference numeral 11 in FIG. 1) have been chosen to be very narrow, lest they interfere with the mechanism of the gradual closing of the valve.

In view of the above, the influence of geometry and material properties of the membrane valve prosthesis on the distribution of stress in the membranes in a closed valve has been determined in the design study.

FIG. 1 diagrammatically illustrates the symmetric membrane valve prosthesis according to the invention in closed position. The membrane valve prosthesis has three synthetic leaflets or membranes 1, which are each provided with fibres 23 extending substantially parallel to each other. Each membrane 2 thereby comprises a free membrane portion 21, which is connected to the basis of the frame 1 and a coaptation area 22, which is connected at its ends to a respective frame leg 11. In closed position the one half of the coaptation area 22 of a membrane 2 bears against a corresponding half of the coaptation area of an adjacent membrane, whilst the other half bears against a respective half of the other adjacent membrane. The angles made by the coaptation areas 22 of the membranes 2 in closed position of the membrane valve prosthesis are 120° each. According to the invention a heart valve prosthesis preferably comprises a frame and three fibre-reinforced membranes suspended in the frame, said frame being substantially an upright, circular closed strip with three frame legs located along the strip at equal distance in the same direction, whereby the height of the strip is greatest near the frame legs and each time decreases symmetrically, according to a predetermined curve, in particular curve z(AB) as referred to on page 5, from two frame legs along the strip to the centre of the strip portion between the frame legs and whereby the coaptation portion of a membrane is connected to two adjacent frame legs and the free membrane portion is connected to the strip portion of the frame enclosed by the frame legs, whereby in the closed position of the heart valve prosthesis the coaptation portions of the membranes lie against each other and the ends of the coaptation portions not connected to the frame legs define a substantially straight line.

Figure 2:
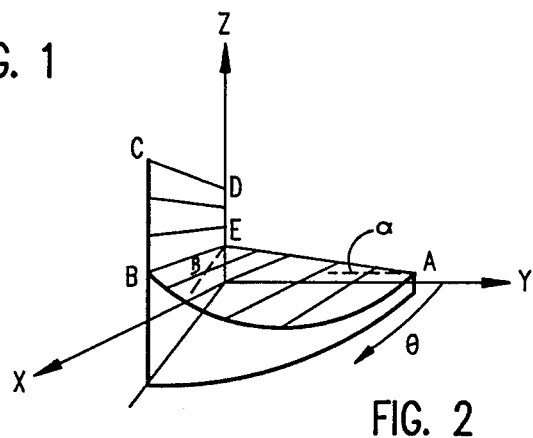
FIG. 2 shows, in a three-dimensional orthogonal coordinate system, one sixth part of the heart valve prosthesis of FIG. 1, comprising a frame leg and a half membrane and being used as an arithmetic model.

In FIG. 2 a diagrammatic view of the basic model of the membrane valve prosthesis is shown. ABE represents hereby the free membrane area 21, whilst BCDE represents the coaptation plane 22; naturally of a half membrane. The numeric model of FIG. 2 is analogous to that of the so-called Hancock-valve (see chapter 5 in "Tissue Heart Valves", published by M. Ionescu, 1979; pp. 178-179). For the description of the geometry of the basic model the angle $\alpha$, the angle $\beta$, the z-coordinate of point A(z)A)) and the length of the lines BC and DE of the aforementioned Hancock-valve of 23 mm are taken and amount to 20°, 15°, 0.5 mm, 5.1 mm and 1.9 mm respectively. With the assumption that AE, BE, BC, CD and DE are straight lines and AB can be represented by:

$$z(AB) = z(A) + C_1 (\bar{r}\theta)^2$$

-continued
$$x^2 + y^2 = \bar{r}^2 \quad \text{with } C_1 = \frac{z(B) - z(A)}{(\bar{r} \cdot \pi/3)^2} ;$$

$z(B)=4.9$ mm; $\bar{r}=10.82$ mm and $z(A)=0.5$ mm, the membrane geometry has been fully described. This description for the line AB has been chosen because with this relation the geometry of AB has been fully described with one parameter ($C_1$), which is also uniquely related to the angle $\alpha$. Besides that, said representation can be applied to higher values of $\alpha$ than with the spherical description.

Analogous to the Hancock-valve a value of 0.4 mm for the matrix or membrane thickness $d_m$ and a value of 1.8 N/mm$^2$ for the elastic modulus or modulus of elasticity was chosen for the basic model.

In table A, in the column with the heading "basic value", the numeric values of the parameters indicated in said table are shown. With these values of the geometric and material parameters the basic model was subjected to a pressure load of 12 kPa effected in 10 ms.

After that, the following four stress parameters were analyzed:
(I) the von Mises-intensity in the membrane portions between fibres to characterise the breaking-down action of the membrane;
(II) the tensile stress in the fibres corresponding with the breaking of the fibres;
(III) the negative values of the minimum principal stress in the coaptation area which represent the wrinkling or creasing of the membrane; and
(IV) the magnitude of the shear force per unit of length between fibre and membranes or matrix as a measure of the tearing loose from the membrane of the fibres.

Figure 3:
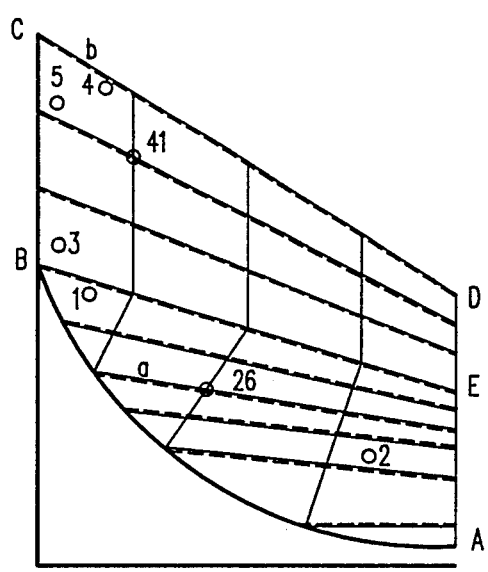
FIG. 3 illustrates the projection of an elementary division of the half membrane of FIG. 2 in the plane of the coaptation area.

The results of this analysis will now be discussed with reference to FIG. 3. The highest values for the von Mises-intensity are found near point B, along the line BC and in the centre of the membrane (from B to line AE), viz. values from 0.12 to over 0.16 (N/mm$^2$). With a further study of the influence of the geometry and material parameters, the points 1-4 in FIG. 3 will be considered with regard to the influence of said parameters on the distribution of stress in the membrane.

For the fibres in the coaptation area the maximum value for the tensile stress in the fibres is found at their fixation to the frame, whereby said value decreases into the direction of the centre of the valve. The tensile stress in the fibres in the free membrane area is substantially constant along the entire length of the fibres. For a further observation the fibre parts a and b of FIG. 3 will be considered.

The largest negative principal stress is found near the fixation of the membrane to the frame in the coaptation area. Points 3 and 5 in FIG. 3 will be taken as representative points for a further analysis. The shear force per unit of length between fibre and membrane has been calculated for the arbitrary system points as 26 in the free membrane area and 41 in the coaptation area and amount to 0.0006 and 0.021 N/mm respectively.

The maximum tensile stress in the fibres was lower than 0.5 N/mm$^2$, whilst the minimum principal stress in the membranes was smaller than $-0.07$ N/mm$^2$.

Therefore, in order to obtain a global insight, the parameters enumerated in Table A were varied between the minimum and maximum values illustrated in the relevant columns, whereby most of these values are chosen rather arbitrarily, yet in such a manner that differences in stresses were expected.

One by one the parameters were varied, without changing the remaining parameters mentioned, between said minimum and maximum value and, in order to obtain a quantitative comparison of the stress situations for the various adjustments of the parameters, points were chosen in the valve geometry where there was the worst distribution of stress in the basic model. Referring to FIG. 3 the von Mises-intensity was therefore determined for the points 1,2,3 and 4, the tensile stress of the fibres was given for the fibre parts a and b, the minimum principal stress was given for the points 3 and 5 and the shear force for the system points 26 and 41.

The aforementioned membrane thickness and modulus of elasticity of the membranes were not varied. They were chosen to ensure lower bending stresses in the membranes, which is considered to be of great importance with regard to the opening and closing action of the membranes. On the other hand, a low value of the membrane thickness is bad because of the desired strength in the closed position, whilst the modulus of elasticity of the membranes cannot be decreased much because of manufacturing reasons, when e.g. polyurethanes are used. As applicable values for said parameters the intervals $0.2 < d_m < 0.6$ mm and $1 < E_f < 5$ N/mm² will be taken. Table B shows the results of these calculations.

From Table B it appears that the parameters that cause the greatest change in the distribution of stress are the parameters $d_{FR}$, $\alpha$, $d_f$, $E_f$ and mfd.

From Table B it can furthermore be read that the highest value of the von Mises-intensity in the membrane is always present in point 1 and slightly less in point 3. The maximum tensile stress in the fibre is not related to a certain fibre portion. The magnitude of the negative minimum principal stress is usually much lower than the van Mises-intensities. The highest negative value is usually found in point 3.

The stress parameters are hardly influenced by the modulus of elasticity of the frame material, the size of the coaptation area and the variation of the viscous properties of the membrane and frame material in the ranges considered. The fibre-stress only changes in the coaptation area.

Finally the behaviour of the five aforesaid geometry and material parameters on the distribution of stress has been studied, whereby mutual influencing has been taken into account.

The remaining five parameters were varied in smaller steps for that purpose.

It has become apparent that with $E_{FR} = 1582$ N/mm², $d_{FR}$ is only of importance if it ranges from 0.6 to 1.4 mm. With a frame thickness of over 1.4 mm no changes in stress are observed. With a frame thickness between 0.6 and 1.4 mm the stresses in the coaptation area (membrane points 3, 4 and fibre part b) increase with an increasing frame thickness. The tensile stress of the fibres in the free membrane area (fibre part a) remains constant then, whereas the membrane stresses in the free membrane area (point 1 and 2) decrease.

An increase of $\alpha$ leads to a decrease of the stresses in the membrane and the fibres in the coaptation area, whereas the changes in the free membrane area are only marginal, with the exception of the von Mises-intensity in point 1, which increases with an increasing $\alpha$.

TABLE A

| symbol | parameter | basic value | minimum value | maximum value |
|---|---|---|---|---|
| $E_{FR}$ | modulus of elasticity of the frame (N/mm²) | 1582 | 1000 | 200,000 |
| $d_{FR}$ | frame thickness (mm) | 1 | 0.5 | 2.5 |
| $\alpha$ | angle in the free membrane area (°) | 20 | 0 | 60 |
| $A_{coap}$ | size of the coaptation area (mm²) | 38.2 | 19.1 | 76.4 |
| $d_f$ | fibre thickness | 0.4 | 0.1 | 0.7 |
| $E_f$ | modulus of elasticity of the fibres (N/mm²) | 23 | 2.3 | 230 |
| mfd | average fibre distance (mm) | 1.4 | 1.4 | (no fibres) |

TABLE B

| | von Mises intensity (N/mm²) | | | | fibres stress (N/mm²) | | negative values of minimum principal stress (N/mm²) | | shear force per unit of length (N/mm²) | |
|---|---|---|---|---|---|---|---|---|---|---|
| | 1 | 2 | 3 | 4 | a | b | 3 | 5 | 26 | 41 |
| basic model | 0.222 | 0.147 | 0.158 | 0.133 | 0.47 | 0.44 | 0.096 | 0.049 | 0.0006 | 0.0206 |
| $E_{FR} = 1000$ N/mm² | 0.227 | 0.151 | 0.157 | 0.106 | 0.48 | 0.41 | 0.097 | 0.050 | 0.0003 | 0.0211 |
| $E_{FR} = 200,000$ N/mm² | 0.210 | 0.141 | 0.161 | 0.128 | 0.45 | 0.51 | 0.092 | 0.046 | 0.0009 | 0.0192 |
| $d_{FR} = 0.5$ mm | 0.219 | 0.118 | 0.088 | 0.027 | 0.33 | 0.05 | 0.000 | 0.016 | 0.0134 | 0.0073 |
| $d_{FR} = 2.5$ mm | 0.211 | 0.141 | 0.161 | 0.128 | 0.46 | 0.51 | 0.092 | 0.046 | 0.0011 | 0.0193 |
| $\alpha = 0°$ | 0.162 | 0.142 | 0.170 | 0.134 | 0.40 | 0.54 | 0.106 | 0.047 | 0.0004 | 0.0185 |
| $\alpha = 60°$ | 0.296 | 0.101 | 0.151 | 0.158 | 0.66 | 0.73 | 0.164 | 0.010 | 0.0339 | 0.0058 |
| $A_{coap} = 19$ mm² | 0.230 | 0.149 | 0.181 | 0.161 | 0.50 | 0.58 | 0.101 | 0.067 | 0.0004 | 0.0295 |
| $A_{coap} = 76$ mm² | 0.212 | 0.145 | 0.134 | 0.055 | 0.45 | 0.22 | 0.079 | 0.023 | 0.0008 | 0.0088 |
| $d_f = 0.1$ mm | 0.270 | 0.186 | 0.208 | 0.202 | 0.66 | 0.87 | 0.099 | 0.034 | 0.0205 | 0.0028 |
| $d_f = 0.7$ mm | 0.177 | 0.121 | 0.123 | 0.069 | 0.30 | 0.20 | 0.087 | 0.053 | 0.0192 | 0.0242 |
| $E_f = 2.3$ N/mm² | 0.267 | 0.184 | 0.204 | 0.195 | 0.07 | 0.08 | 0.099 | 0.036 | 0.0083 | 0.0073 |
| $E_f = 230$ N/mm² | 0.133 | 0.136 | 0.097 | 0.049 | 1.37 | 0.66 | 0.076 | 0.052 | 0.0394 | 0.0207 |
| mfd = ∞ | 0.275 | 0.177 | 0.214 | 0.215 | — | — | 0.099 | 0.032 | — | — |
| "viscous frame" | 0.224 | 0.148 | 0.158 | 0.110 | 0.47 | 0.43 | 0.097 | 0.050 | 0.0006 | 0.0205 |
| "elastic membrane" | 0.237 | 0.166 | 0.169 | 0.117 | 0.49 | 0.45 | 0.105 | 0.054 | 0.0009 | 0.0220 |
| "viscous membrane" | 0.214 | 0.141 | 0.153 | 0.111 | 0.46 | 0.44 | 0.091 | 0.047 | 0.0088 | 0.0198 |

$E_{FR}$ = modulus of elasticity of the frame
$d_{FR}$ = frame thickness
$\alpha$ = angle in the free membrane area
$A_{coap}$ = size of the coaptation area
$d_f$ = fibre thickness
$E_f$ = modulus of elasticity of the fibres
mfd = mean fibre distance If the fibre-thickness increases, the stresses in the membrane and the fibres become smaller across the entire membrane.

Stiffening of the fibres leads to an increase of the tensile stress in the fibres and to a decrease of the von Mises-intensity in the membranes. Finally, the membrane stresses generally show a slight increase with an increase of the average fibre distance. Only for the von Mises-intensity in point 2 (FIG. 3) a relatively discrete line is found when the smallest distance from point 2 to the nearest fibre changes relatively discretely.

There is only a small influence of the design parameters on the negative principal stresses. The angle $\alpha$ and the frame thickness $d_{FR}$ have no influence on the shear forces in the system points 46 and 41, whilst variation of the fibre-stiffness and fibre-thickness leads to a remarkable alteration of the shear forces.

The influence of the average fibre distance on tensile stresses in the fibres and on the shear force is no given. Variation of said design parameters does not provide comparable information about alteration in tensile stress in the fibres and about alterations in shear forces, as the fibrous structure is different for the various cases calculated. Besides the average fibre distance can only have a few discrete values.

The parameter variation study was continued with the four parameters $d_{FR}$, $\alpha$, $d_f$ and $E_f$. For these parameters a statistic procedure was used for obtaining a linear model in which linear interaction terms had been incorporated.

From this it became finally apparent that for the parameter $\alpha$ all stress quantities become smaller for decreasing values of $\alpha$, with the exception of the von Mises-intensity in the points 3 and 4 and the tensile stress in fibre part b. The last-mentioned quantities, however, are substantially smaller than comparable stress quantities in other points of the valve. Therefore, the value of the minimum principal stress is considered a more relevant design criterion for point 3 than the von Mises-intensity at that point; and, therefore the interval $0°<\alpha<20°$ appears to be suitable as an applicable range. With regard to the actual valve design a very small value of $\alpha$ should be avoided to prevent the membrane from giving way in the closed position.

For the quantity $1/d^2_{FR}$ linear relations have been found, as the second order term did not contribute substantially to the linear model. Most stresses show a minimum for $(1/d^2_{FR})\to 0$, which corresponds with a rigid frame. Here the von Mises-intensity in the points 3 and 4 and the tensile stress in fibre part b show an opposite behaviour again. For a rigid frame, however, the values of those stress quantities are substantially lower than the comparable stress quantities in the other points of the valve.

It is surprising that in agreement with the invention it was found that a rigid frame has an advantageous influence on the distribution of stress in the valve. As a result of this a bias in the state of the art that a rigid frame has a disadvantageous influence and the natural situation, viz. a flexible flame, should be preferable, should be abandoned.

For the modulus of elasticity of the fibre material, linear relations are found as well, as the second order term did not contribute substantially to the linear model. The choice of an optimum is made very difficult because a completely different behaviour of the 10 stress quantities was found (i.e. the von Mises-intensities in parts 1-4, the tensile stress in the fibre points a and b, the minimum principal stress in points 3 and 5 and the shear force per unit of length in system points 26 and 41).

Furthermore, starting from $\alpha=10°$ and a rigid frame, $d_f$ and $E_f$ were varied simultaneously in order to specify the fibre design specifications in more detail.

$E_f$ and $d_f$ are varied from 10–50 N/mm$^2$ and 0–1 mm respectively. (In the above $\alpha$ and $1/d^2_{FR}$ were varied between 0°–50° and 0–25 mm$^{-2}$ respectively.)

It has become apparent that the von Mises-intensity in the membranes can be reduced by using a greater fibre stiffness. In that case the tensile in the fibres shows a considerable increase. The highest values of the minimum principal stress were found in point 3. An increase of the fibres stiffness leads to a decrease of that stress quantity, although the change is relatively small.

The shear force in node 26 is relatively high in comparison with node 41 and substantially independent of the fibre stiffness. The shear force in node 41 remains small when $E_f$ ranges from 10 to 50 N/mm$^2$.

Because of that, the value of $E_f$ for the design is to be chosen primarily because of its influence on the von Mises-intensity in membranes and tensile stress in the fibres. As it is plausible that lower membrane stresses are more important with regard to the occurrence of the valve becoming inactive than lower tensile stress values in the fibres, preference is given to higher values of $E_f$. Therefore, the interval $10<E_f<50$ N/mm$^2$ is chosen as an applicable range for $E_f$.

With relation to the choice of the fibre-thickness the applicable values have been restricted to values lower than the matrix thickness. The reason for this is that a thicker membrane in the area of the fibres than between said fibres is disadvantageous with relation to the calcification process. Besides, it is not advisable to increase the value of the membrane thickness because of the bending strains which occur during the opening and closing of the valve. On the other hand, very low values of the membrane thickness lead to higher values of nearly all stress quantities. As a result of that the interval $0.2<d_f<0.3$ mm is chosen as an applicable range for the fibre thickness with a membrane thickness of 0.4 mm.

Finally a rigid frame was chosen for the specific design situation, $\alpha=10°$, $d_m=0.4$ mm, $d_f=0.25$ mm and $E_f=50$ N/mm$^2$, whilst the influence of the fibrous structure on the distribution of stress was analyzed for various values of the average fibre distance mfd.

The difference between the fibre-reinforced basic situation and the situation without fibres (mfd$=\alpha$) lies in the range of 20–75% for all membrane stresses. Reduction of the average fibre distance in the case of fibre-reinforcement, however, leads to much lower values of changes in all stress quantities (lower than 15%). Therefore, the average fibre distance is not very critical by itself. As an applicable range the range $0.8<$mfd$<2.7$ mm is chosen.

In Table C the applicable ranges of the principal parameter values and the chosen value for the design have been indicated or summarized respectively.

TABLE C

|  | applicable range | value chosen |
|---|---|---|
| $E_{FR}$ | 1000 - rigid frame | rigid frame |
| $d_{FR}$ | 0.5–1.5 mm | 1 mm |
| $\alpha$ | 0–20° | 10° |
| $A_{coap}$ | 19–76 mm$^2$ | 38 mm$^2$ |

TABLE C-continued

|  | applicable range | value chosen |
| --- | --- | --- |
| $d_f$ | 0.2–0.3 mm | 0.25 mm |
| $E_f$ | 10–50 N/mm$^2$ | 50 N/mm$^2$ |
| mfd | 0.8–2.7 mm | 1.5 mm |
| $d_m$ | 0.2–0.6 mm | 0.4 mm |
| $E_m$ | 1–5 N/mm$^2$ | 1.8 N/mm$^2$ |

The parameter values given in Table C lead to a valve design that shows various great advantages. As a result of the low α value, the valve has a relatively low height. The great advantage of this is that the valve, implanted in the aorta position, fits to the sinusses, which is important for its closing behaviour. Furthermore, the valve can also be used in the mitral position, whereby a low profile is sometimes necessary because of the lack of space in a small left ventricle. In the latter case the membrane heart valve prosthesis may have two instead of three membranes.

A great advantage of a rigid frame is that steel can be used as frame material, as a result of which problems of the creep of the polymer of a flexible frame can be eliminated. If the frame is made of steel covered with the same material as is used for the membranes, more specifically polyurethane, the membranes may be glued to the frame, which provides a solid attachment. The chosen ratio of fibre stiffness and membrane stiffness is around 25 with a modulus of elasticity of the fibres of 50 N/mm$^2$. The values are within the range of the material parameter values of polyurethanes, which can be produced by standard synthesis techniques. Because of the use of the same material for fibres and membranes, glueing of the two components will ensure a strong fibre-matrix connection. The fibres, having a diameter of 0.25 mm, can be produced by means of spinning techniques. In summary a valve construed in accordance with this invention has a relatively simple design, can be produced in a simple manner and, because of its small height, it can be applied in the aorta and the mitral position.

We claim:

1. Heart valve prosthesis comprising a substantially rigid frame including a base, said frame being provided therein with several synthetic membranes extending across the frame wherein each membrane is a fibre-reinforced matrix material, characterized in that the fibres are arranged in parallel in the matrix material across the membrane and perpendicular to the locus of points forming the commissure line of said membranes and in substantial parallelism with said base and wherein the fibre material and the matrix material are chemically identical.

2. Heart valve prosthesis as claimed in claim 1, characterised in that the matrix material and the fibre material consist of polyether urethane.

3. Heart valve prosthesis as in claim 1 or 2, characterised in that polyether is used for the production of the fibre material, the polyether having a lower molecular weight than the material used for the production of the matrix material.

4. Heart valve prosthesis as claimed in claim 3, characterised in that polyoxy tetramethylene glycol is used for the production of the fibre material, the polyoxy tetramethylene glycol being of a relatively low molecular weight relative to the polymer used for the matrix material.

5. Heart valve prosthesis as claimed in claim 1, whereby the heart value is an aorta valve consisting of three membranes connected to a frame.

6. Heart valve prosthesis comprising a frame and three fibre-reinforced membranes having coaptation and free membrane portions suspended in the frame being substantially an upright, circular closed strip having three equispaced and equidirectional frame legs along the strip and strip portions between adjacent frame legs, the strip having a height being greatest at the frame legs and decreasing symmetrically along the strip from any two adjacent frame legs to the center of the strip portion between the adjacent frame legs in accordance with a predetermined curve, and the coaptation portion of any of the membranes being connected to two adjacent frame legs, whilst the free membrane portion of any of the membranes is connected to the respective strip portion of the frame, whereby in the closed position of the heart valve prosthesis the coaptation portions of the membranes abut each other and the ends of the coaptation portions opposite to and not being connected to the frame legs define a substantially straight line, characterized in that the frame is substantially rigid, that the fibres in the membrane are spaced substantially parallel, that in the closed position of the heart valve prosthesis the fibres in the coaptation portion are substantially perpendicular to said straight line, and that the membranes are connected to the frame directly.

7. Heart valve prosthesis as claimed in claim 6, characterised in that the frame is made of steel.

8. Heart valve prosthesis as claimed in claim 7, characterised in that the thickness of the frame and the diameter of the frame legs are approximately 1 mm.

9. Heart valve prosthesis as claimed in any one of the claims 6, 7 and 8; characterised in that the angle α of the free membrane portion to said line ranges from 0° to 20°.

10. Heart valve prosthesis as claimed in any one of the claims 6, 7 and 8, characterised in that the modulus of elasticity of the fibres in the membranes ranges from 10 to 50 N/mm$^2$.

11. Heart valve prosthesis as claimed in any one of the claims 6, 7 and 8, characterised in that the matrix thickness of the membranes ranges from 0.2 to 0.6 mm.

12. Heart valve prosthesis as claimed in any one of the claims 6, 7 and 8, characterised in that the fibre thickness of the membranes ranges from 0.2 to 0.3 mm.

13. Heart valve prosthesis as claimed in any one of the claims 6, 7 and 8, characterised in that the mean fibre distance in the membranes ranges from 0.8 to 2.7 mm.

14. Heart valve prosthesis as claimed in claim 13, characterised in that the angle α approximately equals 10°, that the modulus of elasticity is approximately 50 N/mm$^2$, that the matrix thickness of the membranes is app. 0.4 mm, that the fibre thickness of the membranes is approximately 0.25 mm and that the average fibre distance in the membranes is approximately 1.5 mm.

15. Heart valve prosthesis as claimed in any one of the claims 6, 7 and 8, characterised in that the surface area of the coaptation portion of the membranes ranges from 38 to 152 mm$^2$ and is preferably 76 mm$^2$.

16. Heart valve prosthesis as claimed in any one of the claims 6, 7 and 8, characterised in that the modulus of elasticity of the matrix material of the membranes ranges from 1 to 5 N/mm$^2$ and is preferably approximately 1.8 N/mm$^2$.

17. Mould for producing a heart valve prosthesis therein, characterised in that the mould is shaped such that a heart valve prosthesis can be produced as indicated in any one of the claims 6, 7 and 8.

* * * * *